(12) United States Patent
Abovitz et al.

(10) Patent No.: US 11,109,917 B2
(45) Date of Patent: Sep. 7, 2021

(54) INTEGRATED SURGERY METHOD AND SYSTEM

(71) Applicant: MAKO Surgical Corp., Ft. Lauderdale, FL (US)

(72) Inventors: Rony Abovitz, Hollywood, FL (US); Hyosig Kang, Weston, FL (US)

(73) Assignee: MAKO Surgical Corp., Ft. Lauderdale, FL (US)

( * ) Notice: Subject to any disclaimer, the term of this patent is extended or adjusted under 35 U.S.C. 154(b) by 153 days.

(21) Appl. No.: 16/522,303

(22) Filed: Jul. 25, 2019

(65) Prior Publication Data

US 2019/0380793 A1 Dec. 19, 2019

Related U.S. Application Data

(63) Continuation of application No. 13/728,800, filed on Dec. 27, 2012, now Pat. No. 10,363,102.

(60) Provisional application No. 61/582,159, filed on Dec. 30, 2011.

(51) Int. Cl.
| | |
|---|---|
| A61B 34/20 | (2016.01) |
| A61B 90/90 | (2016.01) |
| A61B 34/00 | (2016.01) |
| A61B 34/30 | (2016.01) |
| A61B 34/35 | (2016.01) |
| A61B 90/98 | (2016.01) |

(Continued)

(52) U.S. Cl.
CPC ............. *A61B 34/25* (2016.02); *A61B 34/20* (2016.02); *A61B 34/30* (2016.02); *A61B 34/35* (2016.02); *A61B 90/37* (2016.02); *A61B 90/90* (2016.02); *A61B 90/98* (2016.02); *A61B 5/064* (2013.01); *A61B 2034/256* (2016.02)

(58) Field of Classification Search
CPC ................................ A61B 2034/107
See application file for complete search history.

(56) References Cited

U.S. PATENT DOCUMENTS

| | | |
|---|---|---|
| 6,172,941 B1 | 1/2001 | Bieramperl |
| 6,662,036 B2 | 12/2003 | Cosman |
| 7,491,198 B2 | 2/2009 | Kockro |

(Continued)

OTHER PUBLICATIONS

Citeman, Pre-Determined motion time system—PMTS, Apr. 26, 2006, retrieved from the internet at: http://www.citeman.com/436-pre-determined-motion-time-system-pmts.html on Nov. 29, 2015, 2 pages.

*Primary Examiner* — Jacqueline Woznicki
(74) *Attorney, Agent, or Firm* — Foley & Lardner LLP

(57) ABSTRACT

A system for conducting a medical procedure includes a first camera-based 3-D motion sensor configured to generate signals related to the position of a procedure object in the operating room and a controller coupled to the camera-based 3-D motion sensor. The controller is configured to define a predetermined operational plan including positions of a procedure object over time, assign a desired time milestone for each position of the object in the predetermined operational plan, and automatically monitor progress of the procedure based at least in part upon one or more positions of the procedure object over time. The controller is further configured to compare the one or more positions with the desired time milestone, record data relating to an actual time for each position of the object compared with the desired time milestone, and use the data to provide a recommendation for a change to a future predetermined operational plan.

23 Claims, 17 Drawing Sheets

(51) Int. Cl.
*A61B 90/00* (2016.01)
*A61B 5/06* (2006.01)

(56) References Cited

U.S. PATENT DOCUMENTS

| | | |
|---|---|---|
| D616,908 S | 6/2010 | Labak |
| 7,747,311 B2 | 6/2010 | Quaid, III |
| D622,854 S | 8/2010 | Otto et al. |
| 7,799,084 B2 | 9/2010 | Clemow et al. |
| D626,234 S | 10/2010 | Otto et al. |
| 8,206,053 B2 | 6/2012 | Bennett et al. |
| 8,249,345 B2 | 8/2012 | Wu et al. |
| 8,287,522 B2 | 10/2012 | Moses et al. |
| 8,303,575 B2 | 11/2012 | Rodriguez Y Baena |
| 8,347,756 B2 | 1/2013 | Bennett et al. |
| 8,460,277 B2 | 6/2013 | Suarez et al. |
| 8,548,822 B2 | 10/2013 | Moctezuma De La Barrera |
| 2002/0077543 A1 | 6/2002 | Grzeszczuk et al. |
| 2004/0034283 A1 | 2/2004 | Quaid |
| 2006/0190086 A1 | 8/2006 | Clemow et al. |
| 2006/0242096 A1 | 10/2006 | Ozaki et al. |
| 2006/0244593 A1 | 11/2006 | Nycz et al. |
| 2008/0004633 A1 | 1/2008 | Arata et al. |
| 2008/0009697 A1 | 1/2008 | Haider et al. |
| 2008/0183065 A1 | 7/2008 | Goldbach |
| 2008/0262812 A1 | 10/2008 | Arata et al. |
| 2009/0089093 A1 | 4/2009 | Johnson et al. |
| 2009/0177081 A1 | 7/2009 | Joskowicz et al. |
| 2009/0306499 A1 | 12/2009 | Van Vorhis et al. |
| 2009/0314925 A1 | 12/2009 | Van Vorhis et al. |
| 2010/0094429 A1 | 4/2010 | Otto |
| 2010/0110165 A1 | 5/2010 | Iizuka |
| 2010/0153076 A1 | 6/2010 | Bellettre et al. |
| 2010/0256504 A1 | 10/2010 | Moreau-Gaudry et al. |
| 2010/0331670 A1 | 12/2010 | Strommer et al. |
| 2011/0066079 A1 | 3/2011 | Otto et al. |
| 2011/0082462 A1 | 4/2011 | Suarez et al. |
| 2012/0124637 A1 | 5/2012 | Dunaway |
| 2013/0169423 A1 | 7/2013 | Iorgulescu et al. |
| 2013/0172905 A1 | 7/2013 | Iorgulescu et al. |
| 2013/0173008 A1 | 7/2013 | Bechtold et al. |
| 2013/0211421 A1 | 8/2013 | Abovitz et al. |
| 2013/0218137 A1 | 8/2013 | Abovitz et al. |
| 2013/0274769 A1 | 10/2013 | Bonutti et al. |
| 2014/0031664 A1 | 1/2014 | Kang et al. |
| 2014/0186238 A1 | 7/2014 | Holmes et al. |

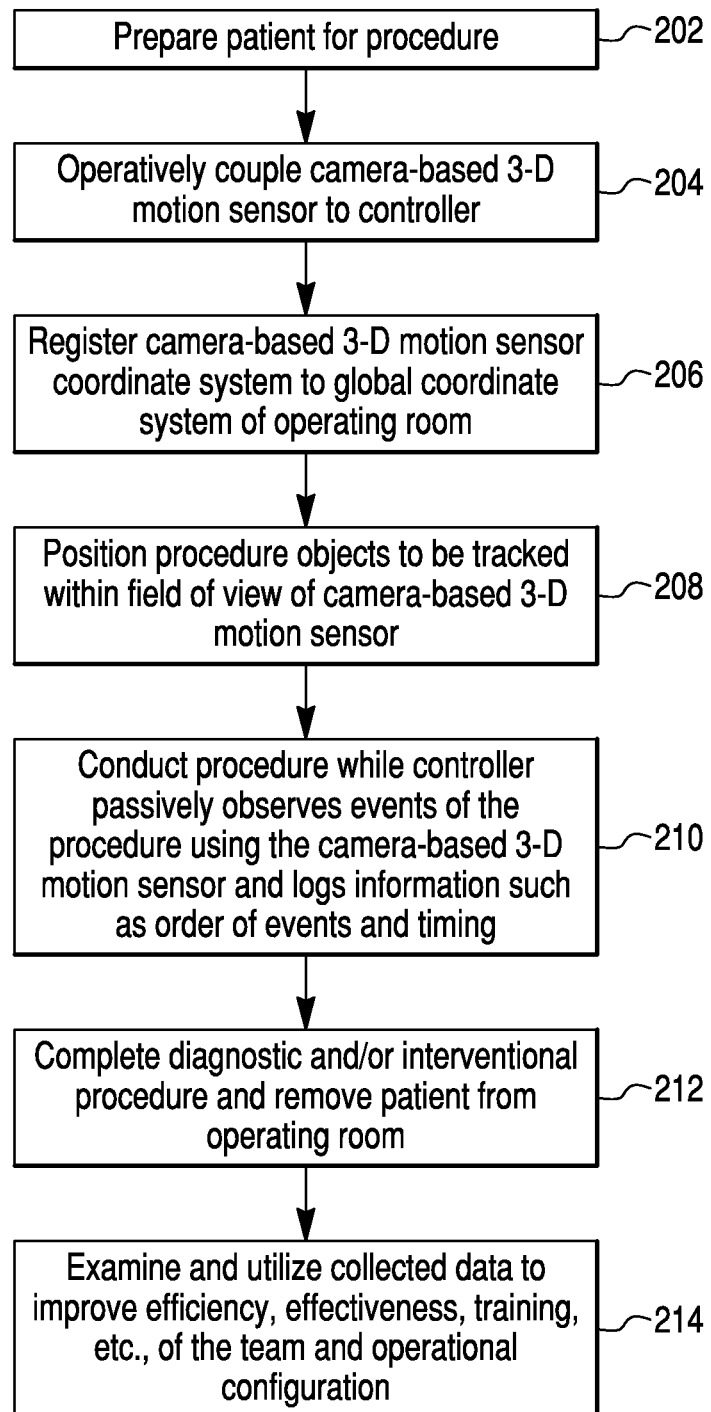

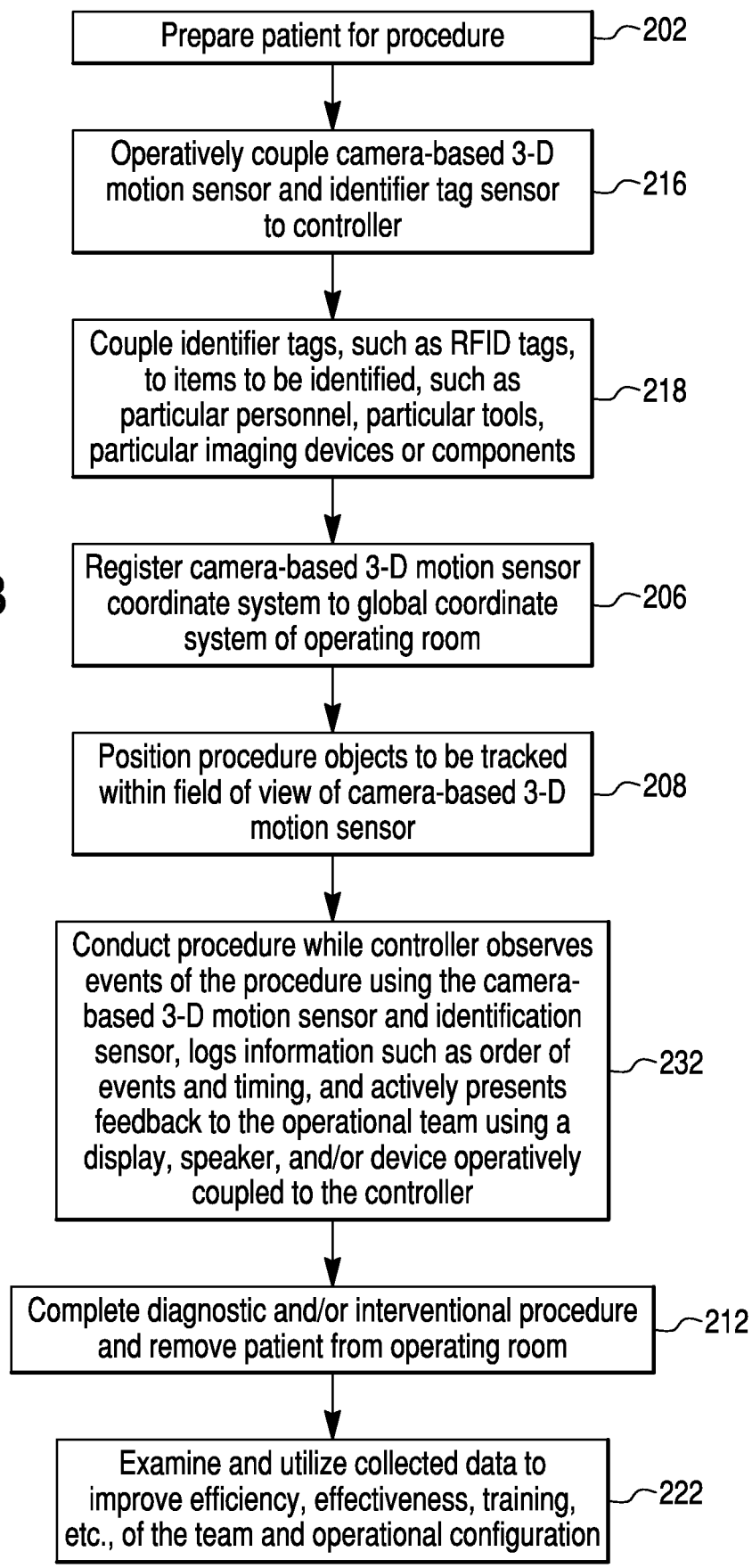

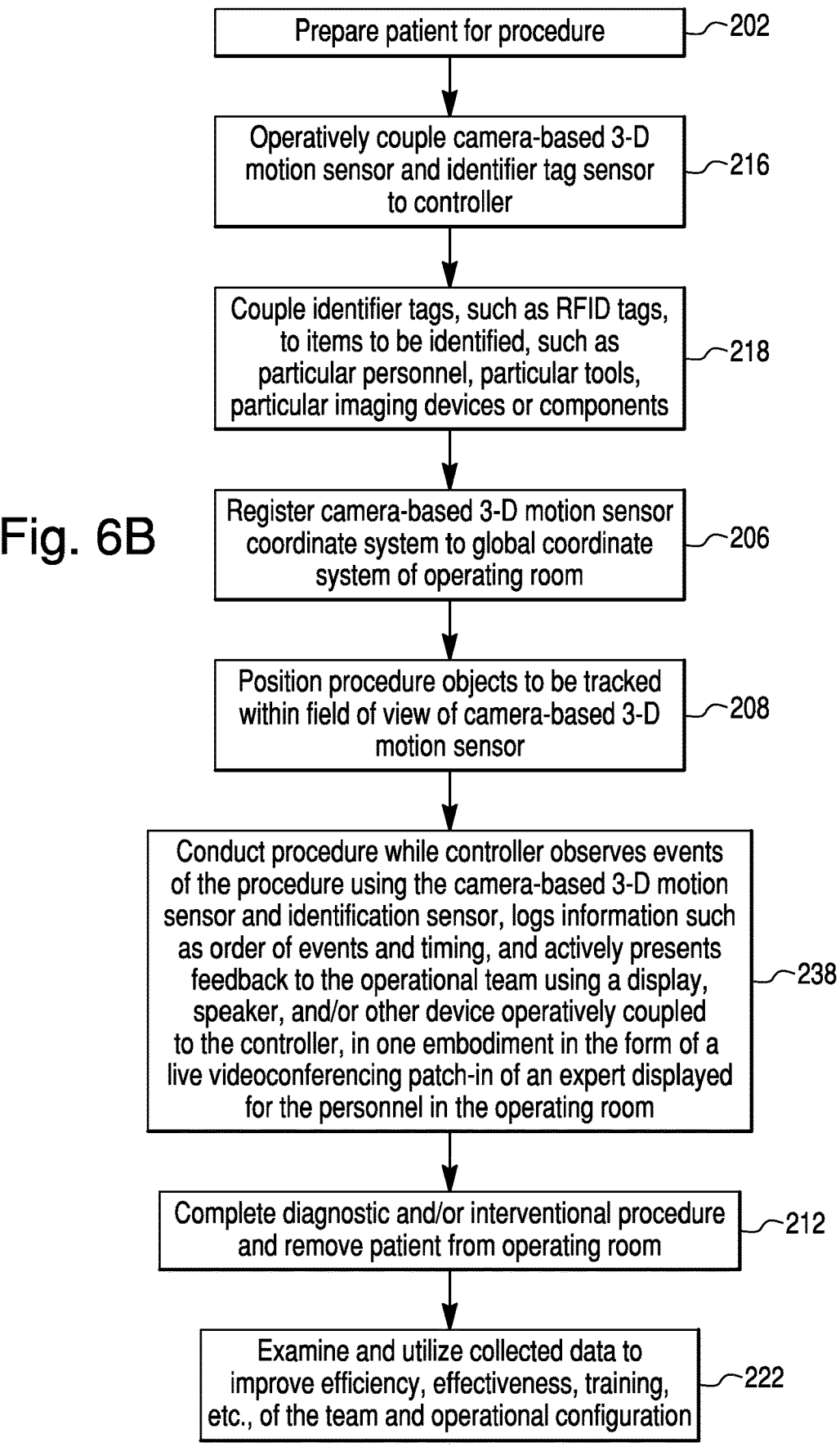

INTEGRATED SURGERY METHOD AND SYSTEM

CROSS REFERENCE TO RELATED APPLICATIONS

The present application is a continuation of U.S. patent application Ser. No. 13/728,800, filed Dec. 27, 2012, which claims the benefit of U.S. Provisional Application No. 61/582,159, filed Dec. 30, 2011, both of which are hereby incorporated by reference herein in their entireties.

FIELD

The present invention relates generally to integrated configurations for conducting diagnostic and interventional procedures in an operating room, and more particularly to systems and methods for monitoring and improving processes and subprocesses of such procedures.

BACKGROUND

Operating room space and time is are two of the most valuable and scare resources of many healthcare systems, and must constantly be optimized to maximize the benefits for the insurers, hospitals, personnel, and patients. With the added complexity of modern technologies utilized in the typical operating room for diagnostic steps, such as imaging, and interventional steps, such as bone cutting in an orthopaedic surgery, specialized pieces of hardware, and specialized teams with specialized training are required. Due to the number of variables presented in such a scenario, there can be a fairly large variability in operating room efficiency and effectiveness. For example, referring to FIG. 1A, a typical operating room configuration is illustrated showing a patient (2) on an operating table (26) with two additional personnel (4, 6) who may be surgeons, assistants, nurses, or the like holding instruments or tools (12, 14 respectively) as they approach the patient to conduct a diagnostic or interventional step of the procedure. An instrument or tool rack or table (28) is shown holding additional instruments (8, 10, 16), and in the depicted configuration, a robotic surgery system (12), such as that sold under the tradename RIO® by MAKO Surgical Corporation of Fort Lauderdale, Fla., features a robotic arm (22) that holds a surgical instrument (20) such as a bone removal burr or saw. Also shown is an optical tracking system (24), such as that sold under the tradename OptoTrak by Northern Digital, Inc. of Ontario, Canada, which may be utilized in association with markers attached to structures to be tracked, such as one or more bones of the patient's body, certain instruments or tools, and/or certain prostheses, reamers, or other structures. To conduct a diagnostic or interventional procedure with such an environment, a predetermined plan or protocol may be developed with best patient results, surgical efficiency, and other factors in mind. For example, referring to FIG. 1B, a desired workflow for accomplishing a given surgical intervention is depicted with sequential procedure steps (30, 32, 34, 36) happening at presumptively ideal or desired time milestones (38, 40, 42, 44) during the procedure. Some procedures, however, do not go exactly as planned, due, for example, to unexpected patient-related challenges, unpredicted instrumentation needs, variability in the skill of the medical team, and the like. In such scenarios, the procedure can vary quite significantly from the planned scenario and timing, and sometimes it is unclear to a particular team what is the most efficient and efficacious way to continue moving forward toward completion of the case. There is a need to simplify and improve the predictability and efficiency of operational workflows, such as that described above in reference to FIG. 1B, to address various factors presented during diagnostic or interventional procedures in the operating room environment. Configurations are presented herein to address this challenge.

SUMMARY

One embodiment is directed to a method for conducting a medical procedure in an operating room, comprising: using a first camera-based 3-D motion sensor mounted in a known position and orientation relative to a global coordinate system of the operating room to generate signals related to the 3-D position of a procedure object in the operating room based upon an outer shape of the procedure object relative to the first camera-based 3-D motion sensor; and automatically monitoring progress of the medical procedure with a controller based at least in part upon one or more positions of the procedure object relative to time as compared with a predetermined operational plan for moving the procedure object over time, the one or more positions based at least in part upon the signals from the first camera-based 3-D motion sensor. The method further may comprise determining the position and orientation of the first camera-based 3-D motion sensor relative to the global coordinate system of the operating room based upon signals generated from a second sensor configured to generate the signals based upon repositioning or reorientation of the first camera-based 3-D motion sensor relative to an established registration position and orientation of the first camera-based 3-D motion sensor relative to the global coordinate system of the operating room. The second sensor may comprise an accelerometer. The second sensor may comprise a joint motion encoder. The method further may comprise operating the controller to adapt automatically to a change detected in the progress of the medical procedure by comparing the monitored progress with a version of the predetermined operational plan that is modified in accordance with the detected change. The version of the predetermined operational plan that is modified in accordance with the detected change may be based at least in part upon a predetermined workflow logic schema. The predetermined workflow logic schema may be based at least in part upon previous surgical experience. The predetermined workflow logic schema may be based at least in part upon input from an expert. The expert may be located remote to the operating room. The method further may comprise providing a video conferencing interface to allow the expert to visualize and communicate with persons located in the operating room. The method further may comprise transmitting one or more images from the first camera-based 3-D motion sensor to the remote expert over the video conferencing interface using a network connection. The method further may comprise providing one or more instrument identifying sensors coupled to one or more instruments within the operating room and operatively coupled to the controller, and identifying with the controller the one or more instruments based at least in part upon the one or more instrument identifying sensors. The one or more instrument identifying sensors may comprise RFID tags. The method further may comprise providing one or more personnel identifying sensors coupled to one or more personnel within the operating room and operatively coupled to the controller, and identifying with the controller the one or more personnel based at least in part upon the one or more personnel identifying sensors. The one or more personnel identifying sensors may comprise RFID tags. The method further may comprise providing one or more patient identifying sensors coupled to a patient within the operating room and operatively coupled to the controller, and identifying with the controller the patient based at least in part upon the one or more patient identifying sensors. The one or more patient identifying sensors may comprise RFID tags. The method further may comprise providing an instrument tracker configured to monitor a position of a procedure object in the operating room based upon detection of reflected radiation from one or more markers coupled to the procedure object, the radiation emitted from the instrument tracker. The one or more markers may comprise reflective spheres or discs. The procedure object may be selected from the group consisting of: a surgical instrument, an imaging system component, an instrument table, and an operating table. The procedure object may be a surgical instrument selected from the group consisting of: a manual surgical hand tool, an electromechanical surgical hand tool, and a pneumatic surgical hand tool. The procedure object may be an imaging system component selected from the group consisting of: an X-ray source; an X-ray detector; and X-ray source-detector coupling member; an ultrasound transducer; a light source; a light detector; a magnetic field source; and a magnetic field detector. The method further may comprise providing an instrument table comprising a touch and object recognition surface operatively coupled to the controller to facilitate identification of objects placed upon the surface. The method further may comprise visually highlighting one or more objects that have been placed upon the surface with the touch and object recognition surface.

BRIEF DESCRIPTION OF THE DRAWINGS

FIG. 4A illustrates a technique for executing a procedure using an integrated system in accordance with the present invention.

FIG. 5B illustrates a technique for executing a procedure using an integrated system in accordance with the present invention.

FIG. 6B illustrates a technique for executing a procedure using an integrated system in accordance with the present invention.

DETAILED DESCRIPTION

Figure 1A:
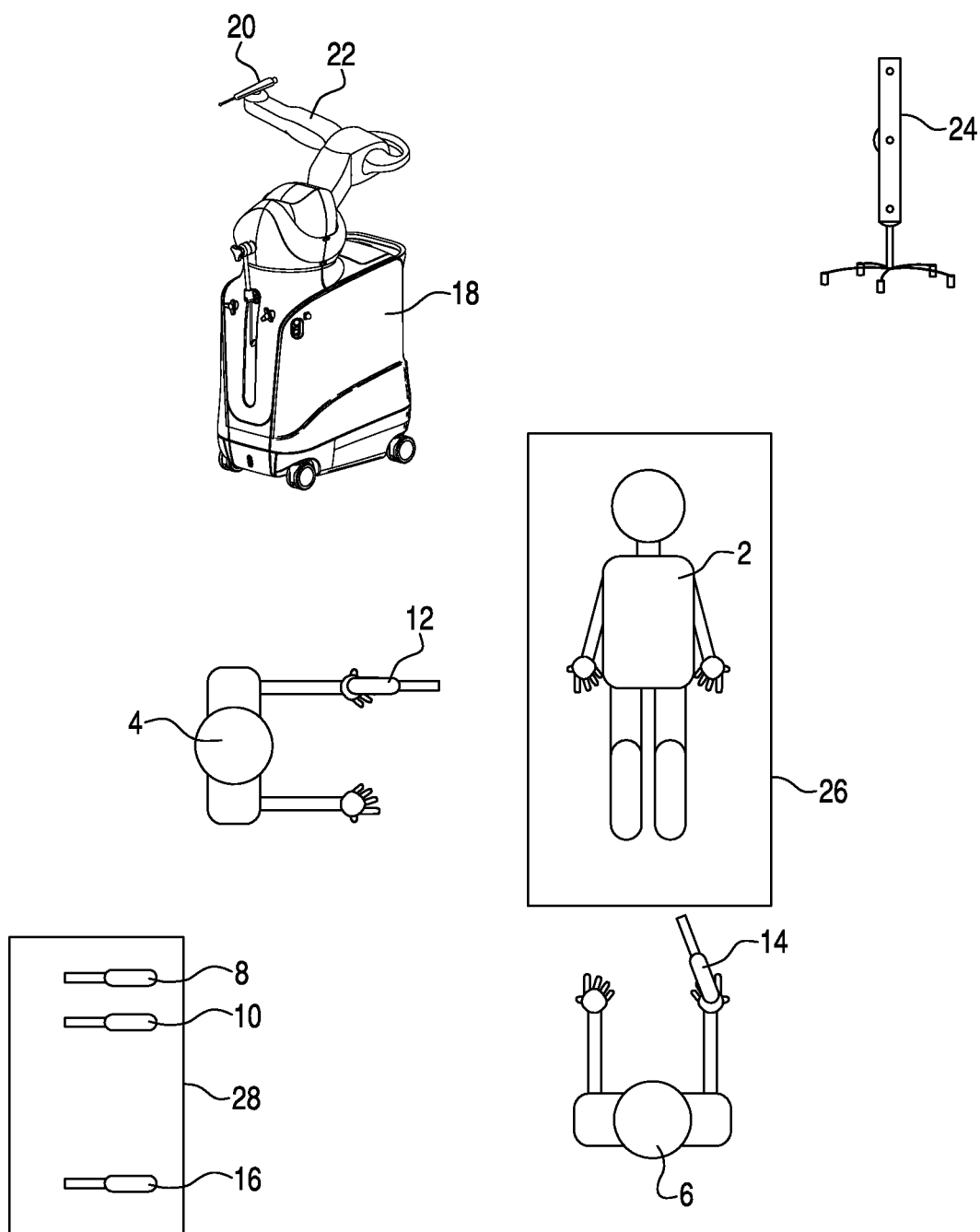
FIG. 1A illustrates a conventional operating room scenario with a robotic surgical system.
Figure 1B:
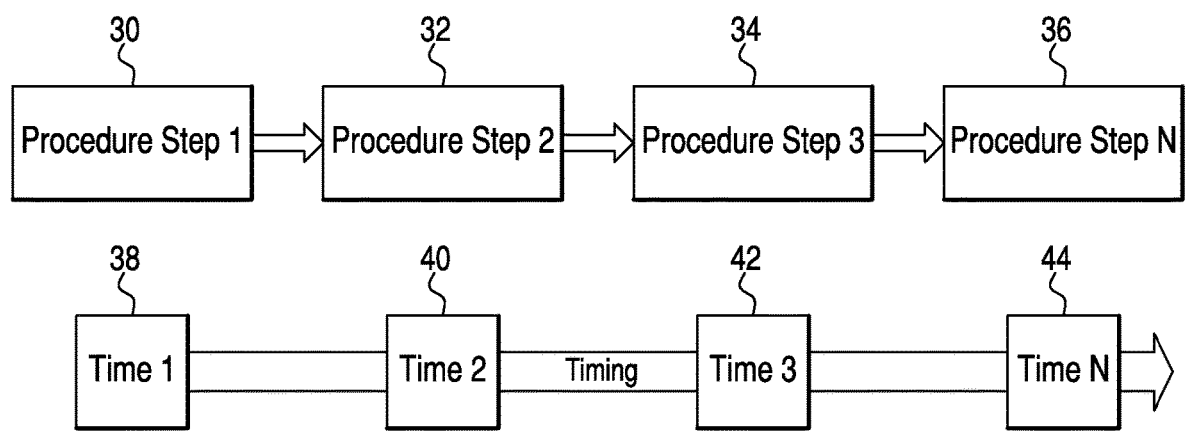
FIG. 1B illustrates a high level procedure plan and timing diagram.
Figure 2A:
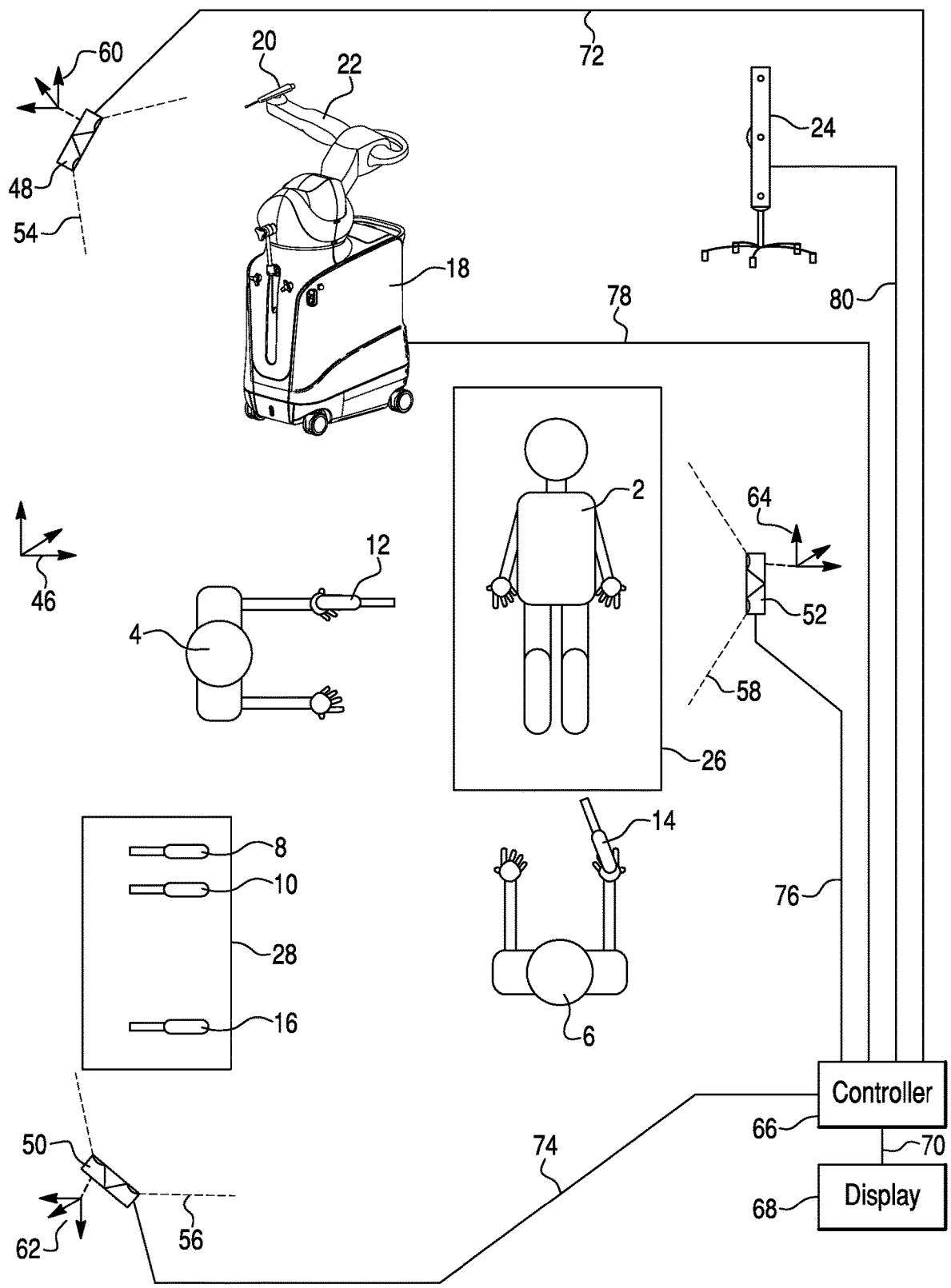
FIGS. 2A-2C illustrate embodiments of integrated system configurations in accordance with the present invention.

Referring to FIG. 2A, an embodiment is depicted wherein one or more camera-based three-dimensional motion sensors (48, 50, 52) may be utilized to track in three dimensions the positions and/or orientations of various hardware components within the fields of view (54, 56, 58) of these sensors. Suitable camera-based three-dimensional motion sensors are available from Microsoft Corporation of Redmond, Wash. under the tradename Kinect®, or from OcuSpec, Inc., of San Francisco, Calif., and are capable of measuring three dimensional (i.e., including depth relative to the perspective of the cameras in their coordinate systems 60, 62, 64) with a relatively high degree of accuracy—and without fidicials or reflective markers, as is generally the case with other optical tracking technologies, such as the depicted and aforementioned optical tracker (24). With a plurality of camera-based three-dimensional motion sensors (48, 50, 52) oriented and placed to have converging fields of view (54, 56, 58), as shown in FIG. 2A, many elements of the surgical environment may be tracked in real or near-real time, including the positions and/or orientations of tools (8, 10, 12, 14, 16) and other structures, such as a hospital bed (26), tool table (26), robotic surgery system (18), robotic arm (22), associated tool (20), or even aspects of the patient (2) or personnel (4, 6) anatomy. The camera-based three-dimensional motion sensors preferably are operatively coupled, such as by a lead wire (72, 74, 76) or wireless connection, to a controller (66), such as a computing workstation, which may be operatively coupled (70) to a display (68) and configured to monitor the positions, orientations, movements, and timing of various elements of the medical procedure at hand, subject to an initial registration process by which the coordinate systems (60, 62, 64) of the structures containing the tracking cameras of the one or more camera-based three-dimensional motion sensors (48, 50, 52) are characterized relative to a global coordinate system (46) of the operating room (i.e. to provide for mathematical transformation between coordinate systems and therefore mathematically relationships between them). The camera-based three-dimensional motion sensors (48, 50, 52) may be fixedly mounted to the ceiling or other structure of the operating room, or may be movably mounted, in which case sensors such as accelerometers, joint encoders may be utilized to maintain a determinable geometric relationship between the sensor position/orientation and the operating room global coordinate system (for example, in the case of an articulating arm with joints and joint encoders that couples a camera-based three-dimensional motion sensor to the operating room). In the depicted embodiment wherein a robotic surgery system (18) is included, such system is operatively coupled (78) to the controller, as is (80) the depicted optical tracking system (24).

Figure 2B:
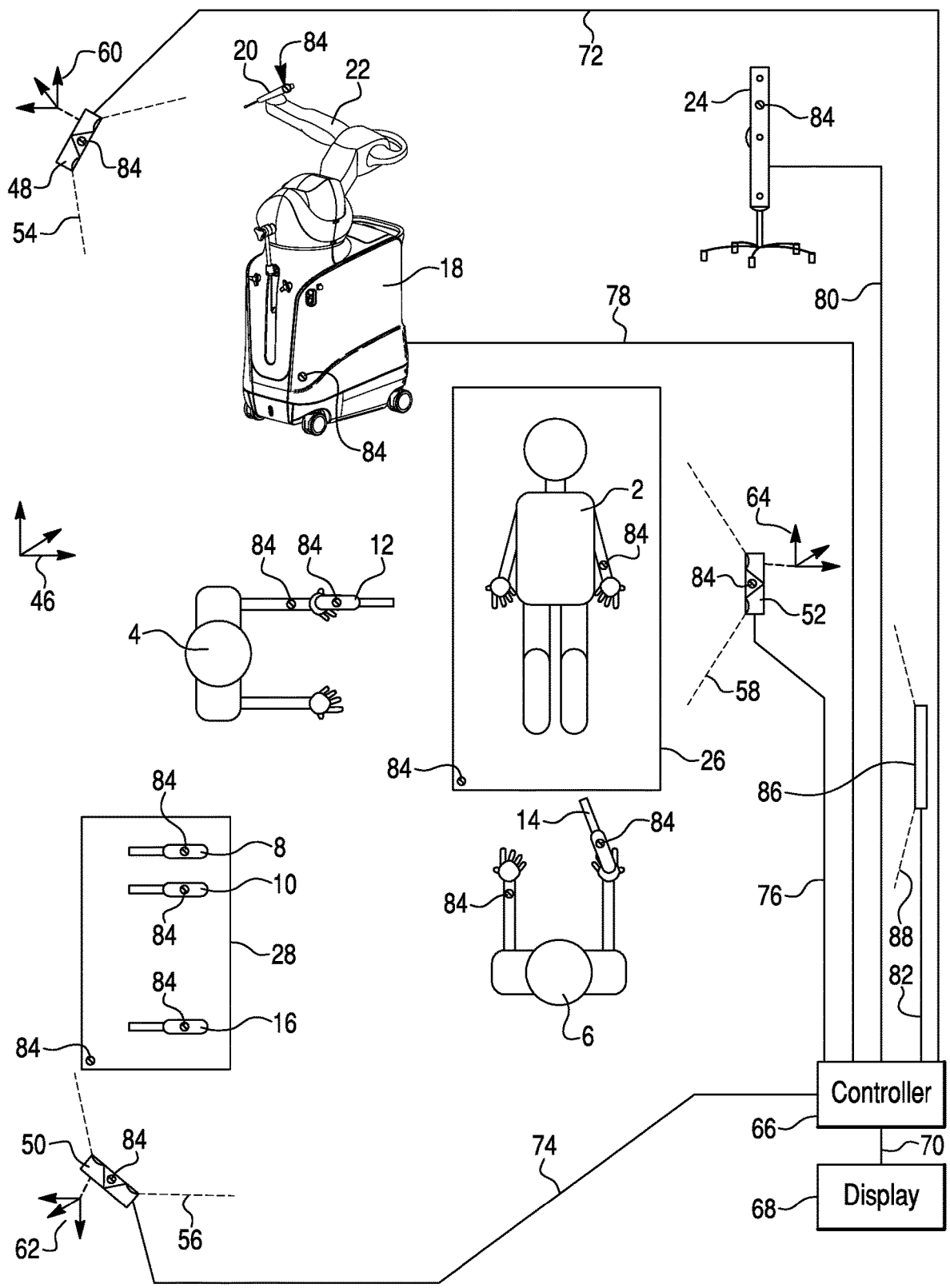

Referring to FIG. 2B, an another embodiment, an identification sensor (86), in the depicted embodiment with a sensing zone (88) akin to a camera's field of view, may be added and operatively coupled (82) to the controller (66) to facilitate not only tracking of elements within the pertinent fields of view (54, 56, 58), but also identification of the particular elements. In one embodiment, RFID technology may be utilized, with an RFID sensor (86) and RFID tags (84) coupled to various structures or "procedure objects" pertinent to the operational theater. For example, in the embodiment illustrated in FIG. 2B, RFID tags (84) are coupled to the instruments (8, 10, 12, 14, 16), the instrument table (28), the operating table (26), the patient (2), each of the other personnel (4, 6), each of the camera-based three-dimensional motion sensors (48, 50, 52), the optical tracking system (24), the robotic surgical system (18), and the associated robotic surgical system instrument (20). With such a configuration, the controller may not only monitor what various elements within the fields of view are doing in terms of movement and/or reorientation, but also which elements are which in terms of affirmative identification.

Figure 2C:
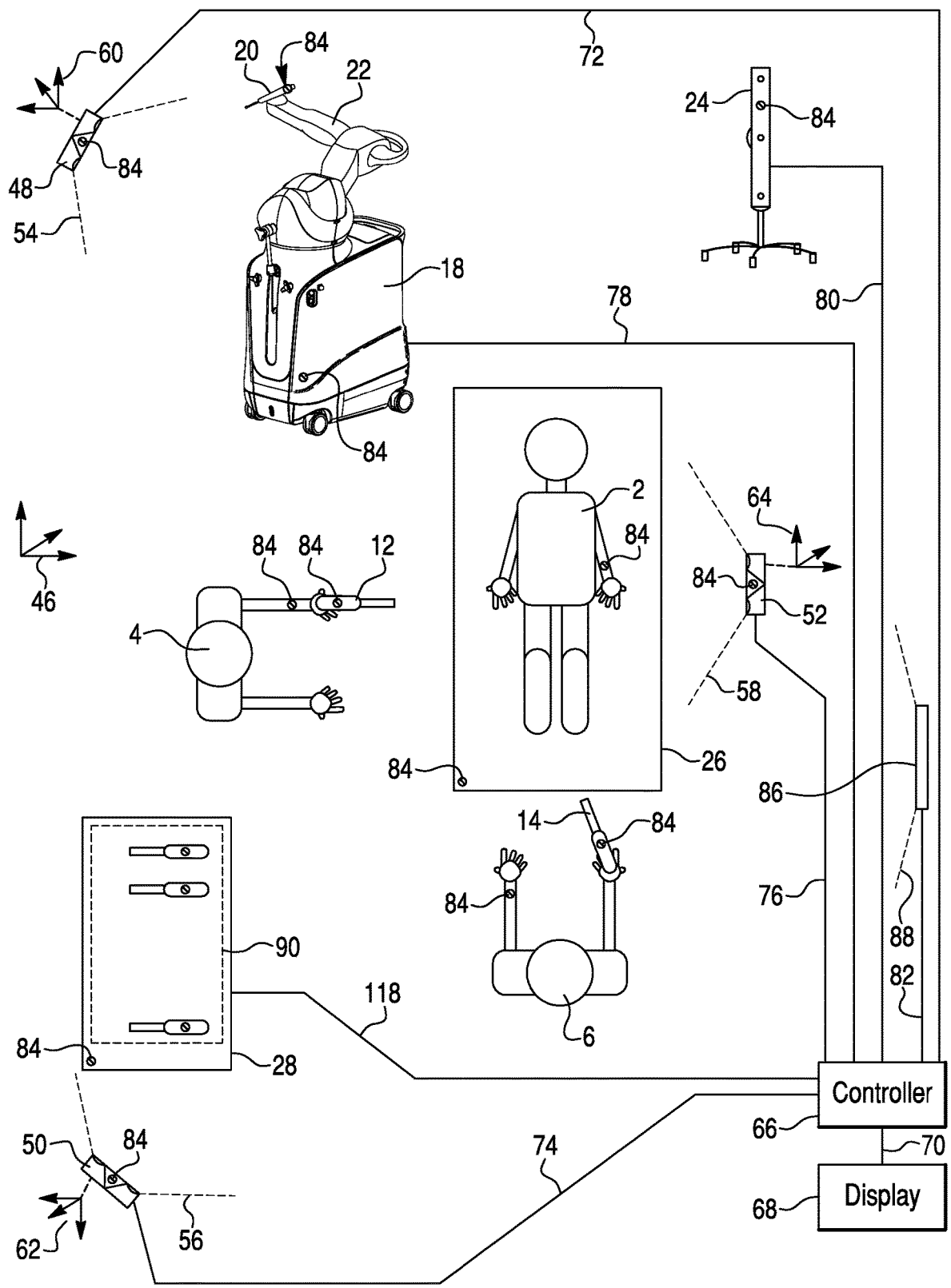

Referring to FIG. 2C, a configuration similar to that of FIG. 2B is illustrated, with the exception that the operating table (28) of the embodiment of FIG. 2C features SmartSurface® technology, as available from Microsoft and Samsung corporations, to provide a surface which not only may be utilized to sense what items are touching it, but also the shapes of these items; further, the SmartSurface, preferably operatively coupled (118) to the controller (66), may be utilized to signal the associated personnel, for example, by placing an illumination highlight below the next tool that should be picked up in accordance with the predetermined operational workflow. Further, the table (28) may feature a speaker or other sound emitting device that may be utilized to signal an operator that a SmartSurface (90) has something to add regarding the procedure (i.e., the next tool to be picked up in accordance with the predetermined workflow may be visually highlighted by the underlying SmartSurface 90, and a beep or other sound may be utilized to get the attention of the personnel in the room so that they look over to the table).

Figure 3A:
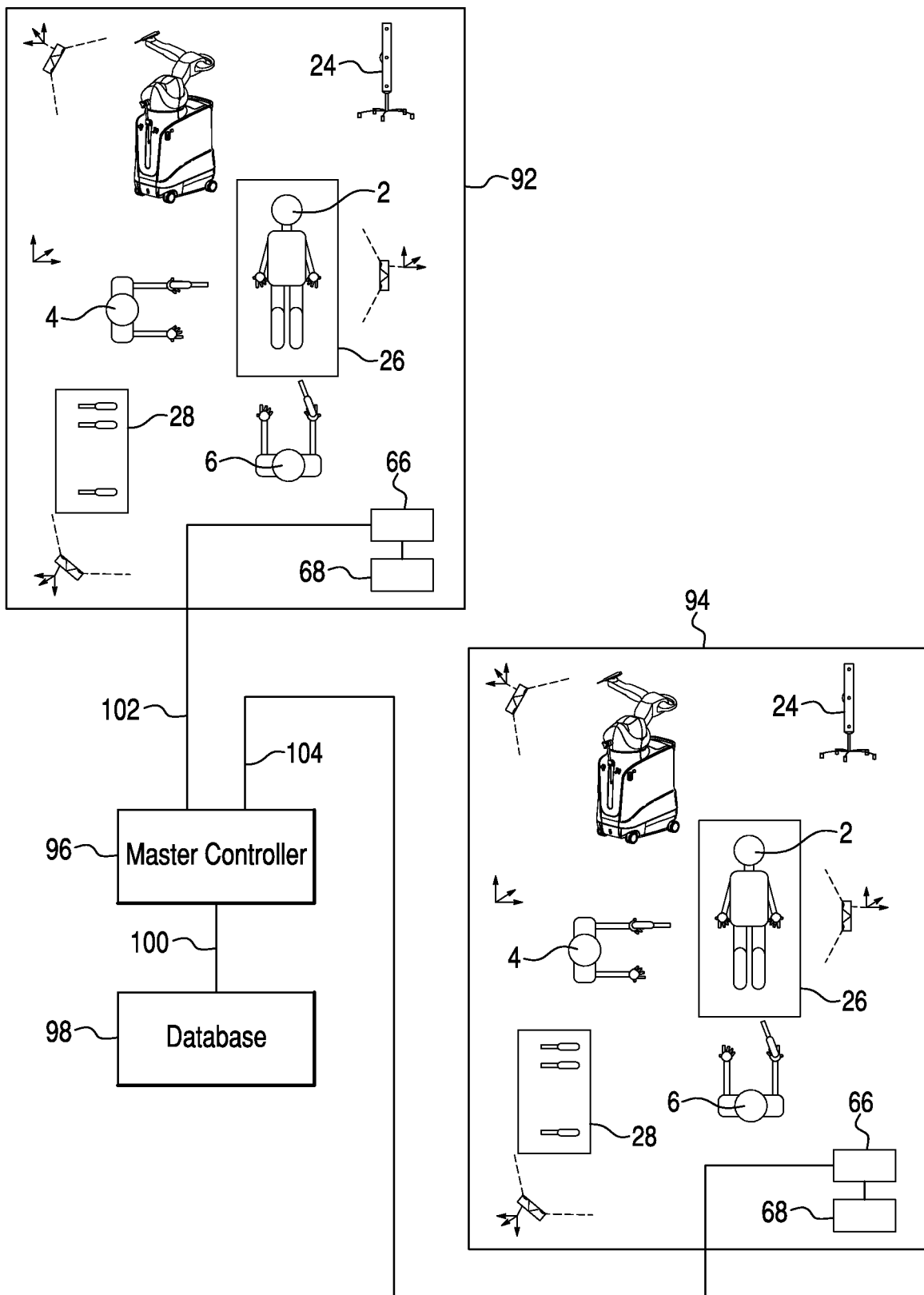
FIGS. 3A-3C illustrate embodiments of high-level integrated system configurations in accordance with the present invention.

Referring to FIG. 3A, a master controller (96), such as a computer workstation operatively coupled (100) to a database (98), may be utilized to provide a higher level of control and centralized processing and/or information flow connectivity (102, 104) to a plurality of operating rooms in a single hospital, or multiple locations. The master controller and database may be located at the same location as one or more of the intercoupled operating rooms, or may be located in a remote location and connected, for example, by the internet. For example, referring to FIG. 3B, in one embodiment, three hospitals with four total connected operating rooms (92, 94, 110, 112) may be operatively coupled (102, 104, 114, 116) via the internet or other networking configuration. Element 106 is utilized to illustrate a boundary between two locations (i.e., in the embodiment illustrated in FIG. 3B, the three hospitals and master controller (96)/database (98) are in different locations to illustrate that all of the assets need not be local to each other.

Figure 3B:
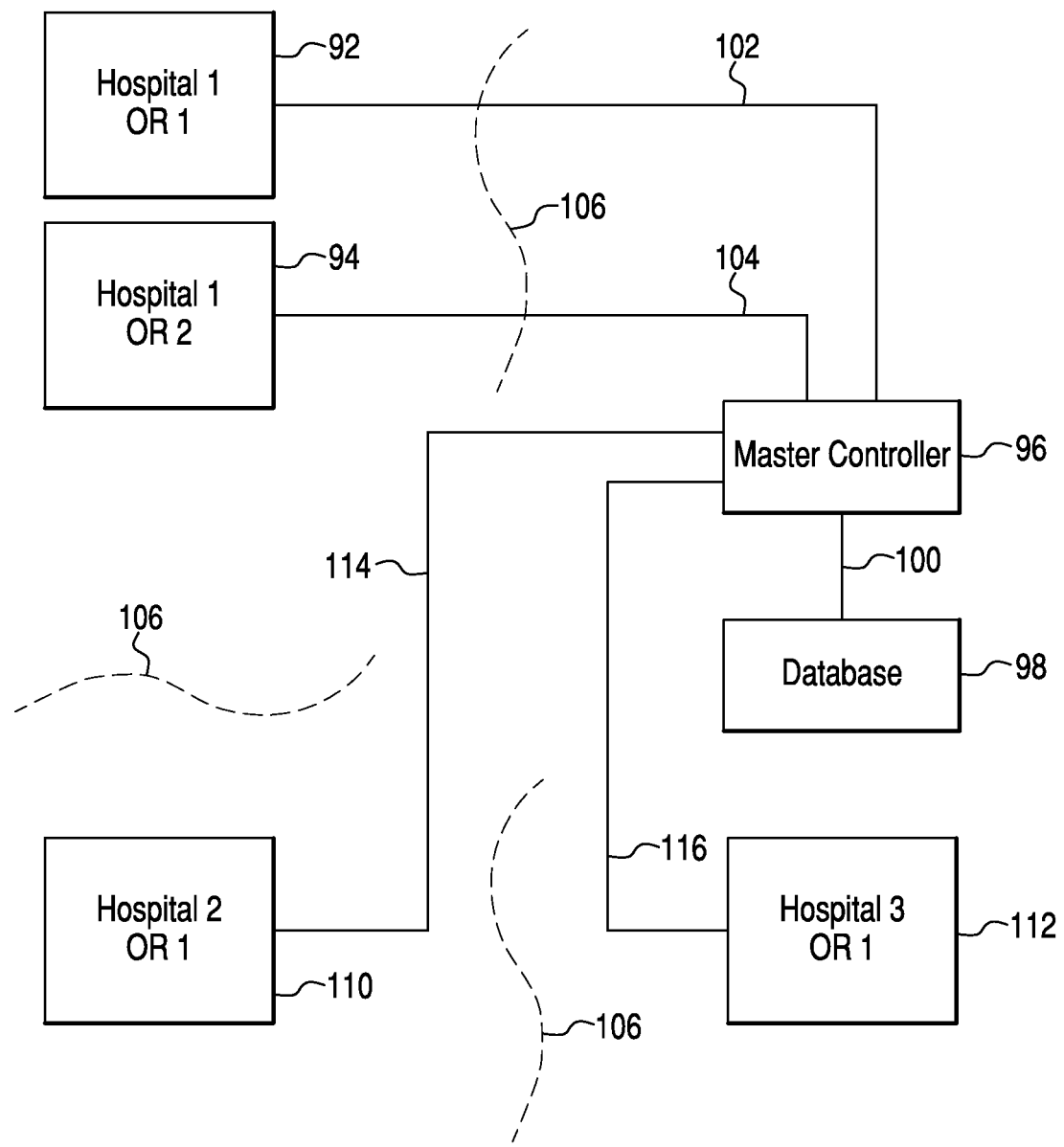
Figure 3C:
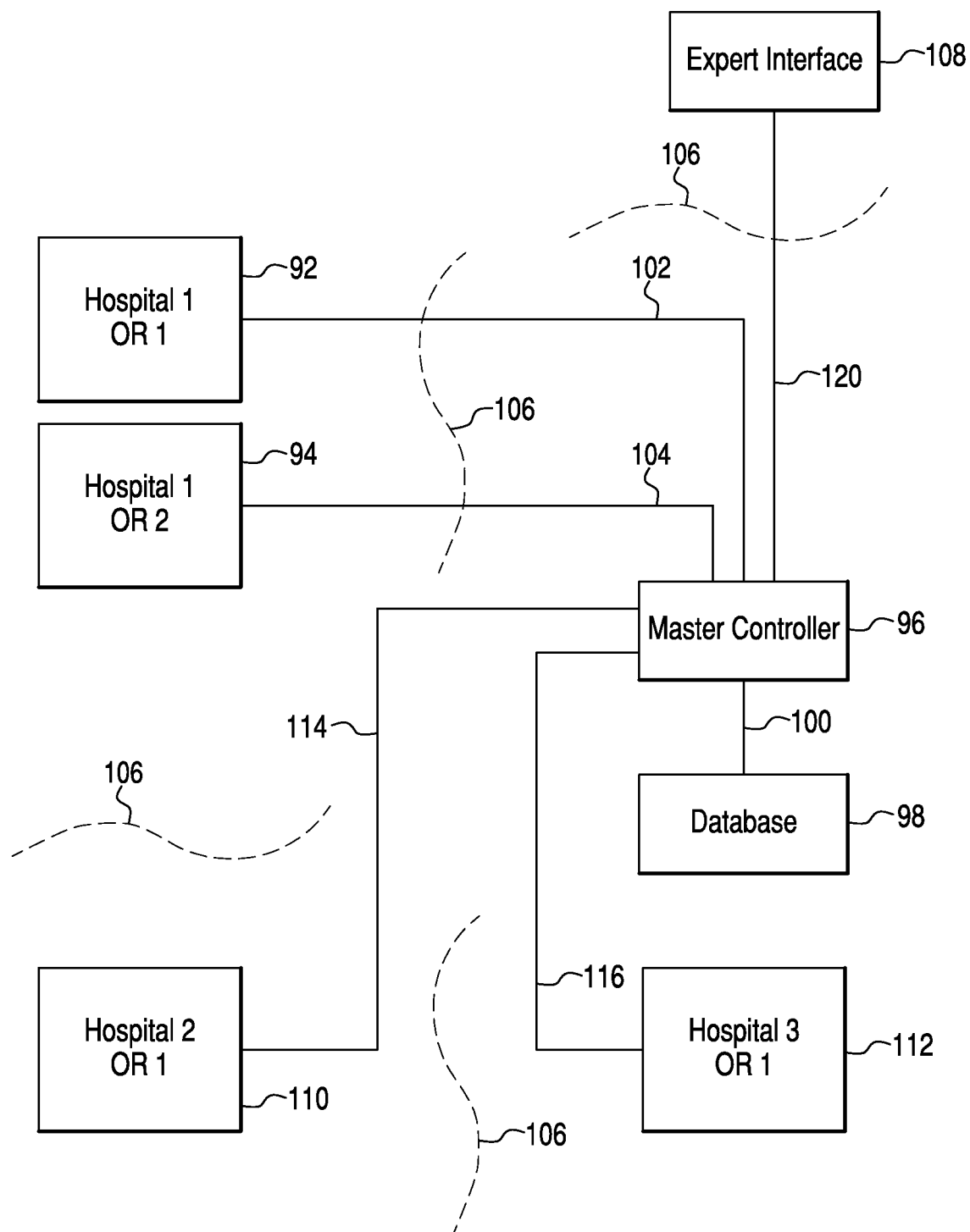

Referring to FIG. 3C, an embodiment similar to that of FIG. 3B is depicted, with the exception that the embodiment of FIG. 3C features an interconnected (120) expert interface subsystem (108), such as those available from the Tandberg/VideoConferencing division of Cisco Systems of San Jose, Calif. under the tradename Cisco Telepresence®, which may be configured to allow an expert (i.e., such as a particular surgical expert, an expert on a particular diagnostic or interventional tool that may be of interest in the procedure in the interconnect operating room, etc) or other person to transiently "join" a portion of an operating room procedure, for example, by using the display (68) intercoupled to the controller (66) local to each of the operating room scenarios of FIGS. 2A-2C.

Referring to FIG. 4A, in one embodiment, a configuration such as those described above in reference to FIGS. 2A-3C may be utilized in a medical procedure. With the patient prepared for the diagnostic and/or interventional procedure (202), one or more camera-based three-dimensional motion sensors operatively coupled to a controller (204), and the coordinate systems of the camera-based three-dimensional motion sensor and operating room registered (206) so that the sensors may be utilized to accurately track positions and/or orientations of various structures of interest relative to the operating room (and patient, who presumably is resting relatively stably on an operating table which is in a locked position relative to the floor of the operating room), the medical procedure may be conducted (210) while the operatively coupled controller utilizes the various sensors to passively observe events and keep track of pertinent information, such as the order of events during the procedure, timing thereof, etc. This information may be utilized during or after (214) the procedure has been completed (212) to improve procedural efficiency, effectiveness, training, and other factors relative to the performance of the team and related systems for the patient care scenario.

Figure 4B:
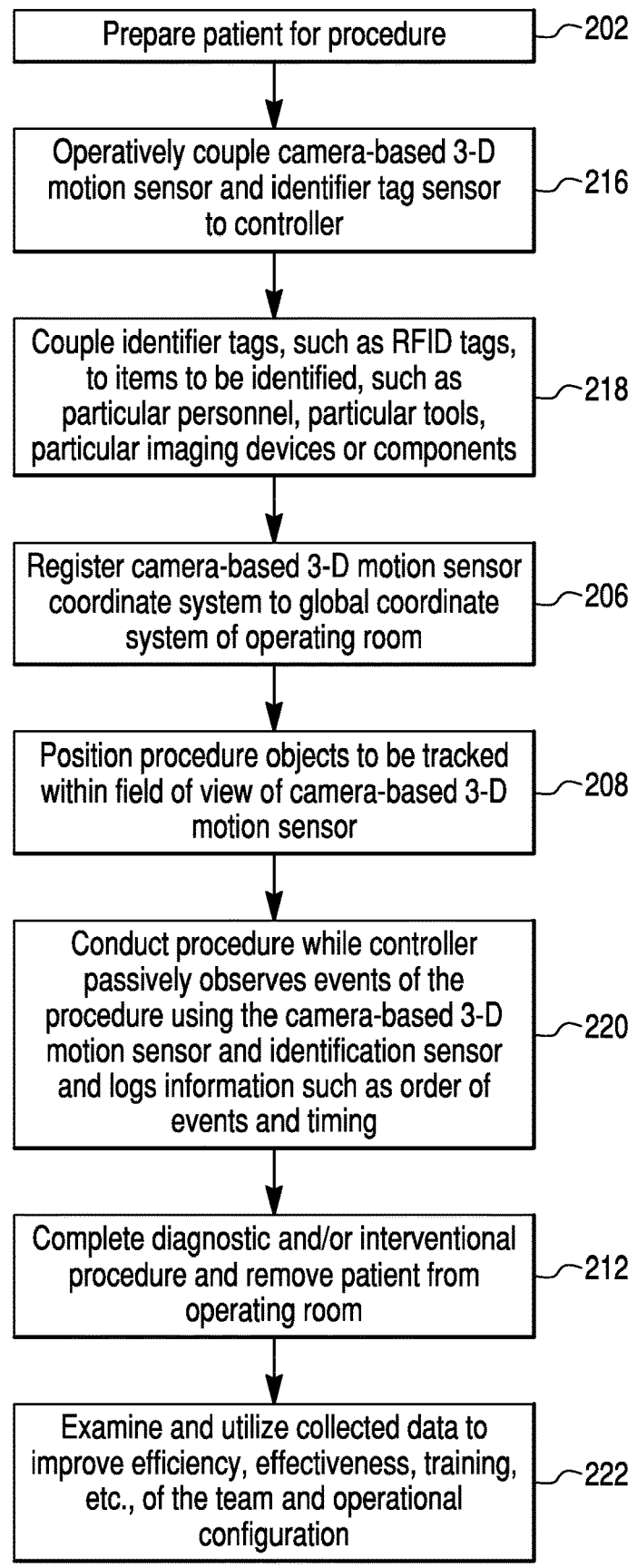
FIG. 4B illustrates a technique for executing a procedure using an integrated system in accordance with the present invention.

Referring to FIG. 4B, in one embodiment, a configuration such as those described above in reference to FIGS. 2A-3C may be utilized in a medical procedure. The embodiment of FIG. 4B differs from that of FIG. 4A in that it includes the use of an identifier tag sensor (216), such as an RFID sensor, which may be utilized along with identifier tags, such as RFID tags, coupled to various structures or objects pertinent to the procedure (218) to identify the objects while they are being tracked during the procedure (220). This additional data may be utilized to assist with improving procedural efficiency, effectiveness, training, and other factors relative to the performance of the team and related systems for the patient care scenario (222).

Figure 4C:
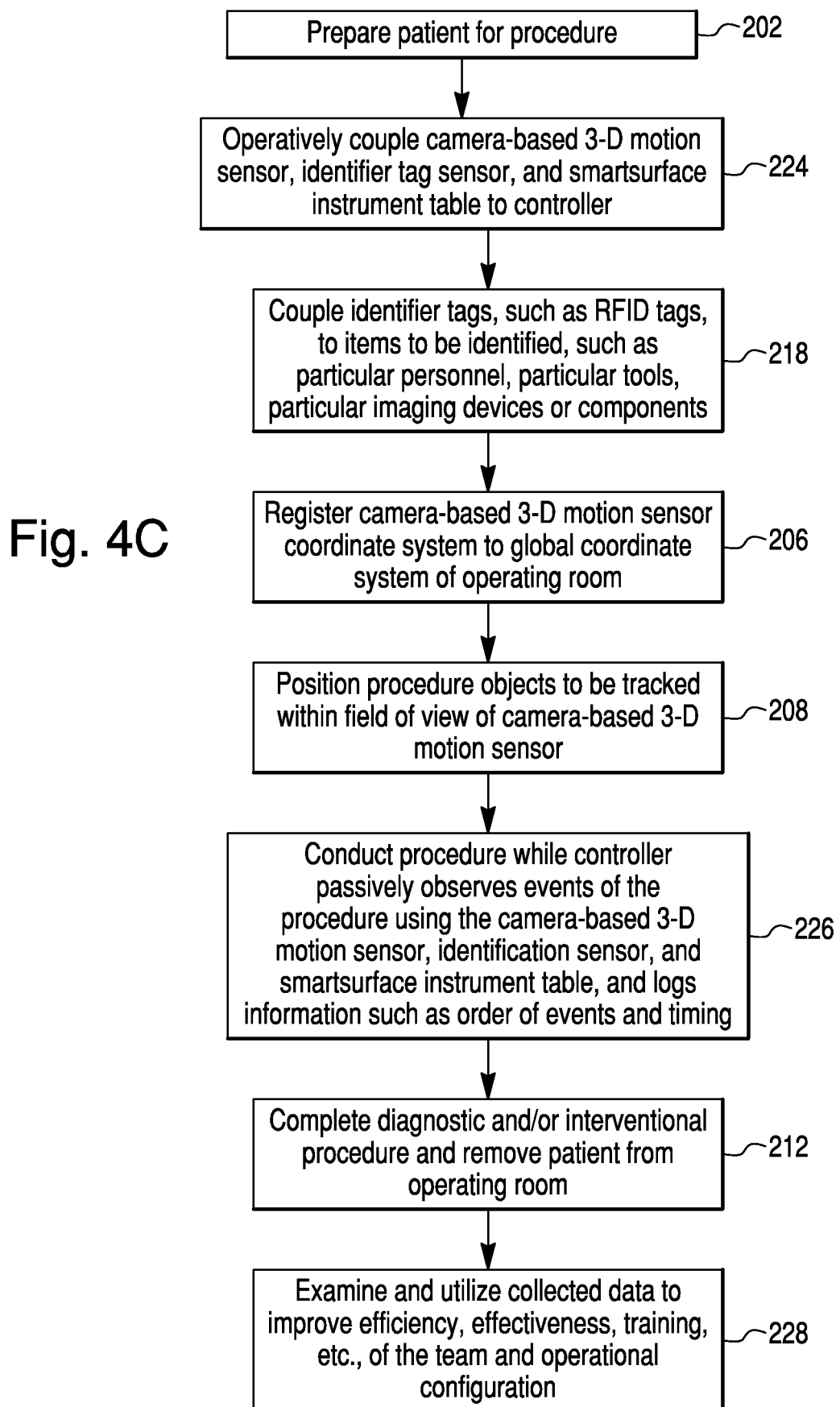
FIG. 4C illustrates a technique for executing a procedure using an integrated system in accordance with the present invention.

Referring to FIG. 4C, in one embodiment, a configuration such as those described above in reference to FIGS. 2A-3C may be utilized in a medical procedure. The embodiment of FIG. 4C differs from that of FIG. 4B in that it includes the use of a smartsurface, such as in an application of a tool or instrument table surface (224). During the procedure, the intercoupled controller may observe the events of the procedure using the camera-based three-dimensional motion sensor, the identification sensor, and the smartsurface device (226), and all of this data may be utilized to assist with improving procedural efficiency, effectiveness, training, and other factors relative to the performance of the team and related systems for the patient care scenario (228). For example, in one illustrative scenario, the data may be utilized to determine that a new scrub nurse does not know the prescribed surgical workflow of a given procedure very well, and is fairly consistently reaching for the wrong tool from the smartsurface tool or instrument table. This data may be utilized to assist in training the new scrub nurse, or in changing the workflow so that it is more intuitive or otherwise more efficient.

Figure 5A:
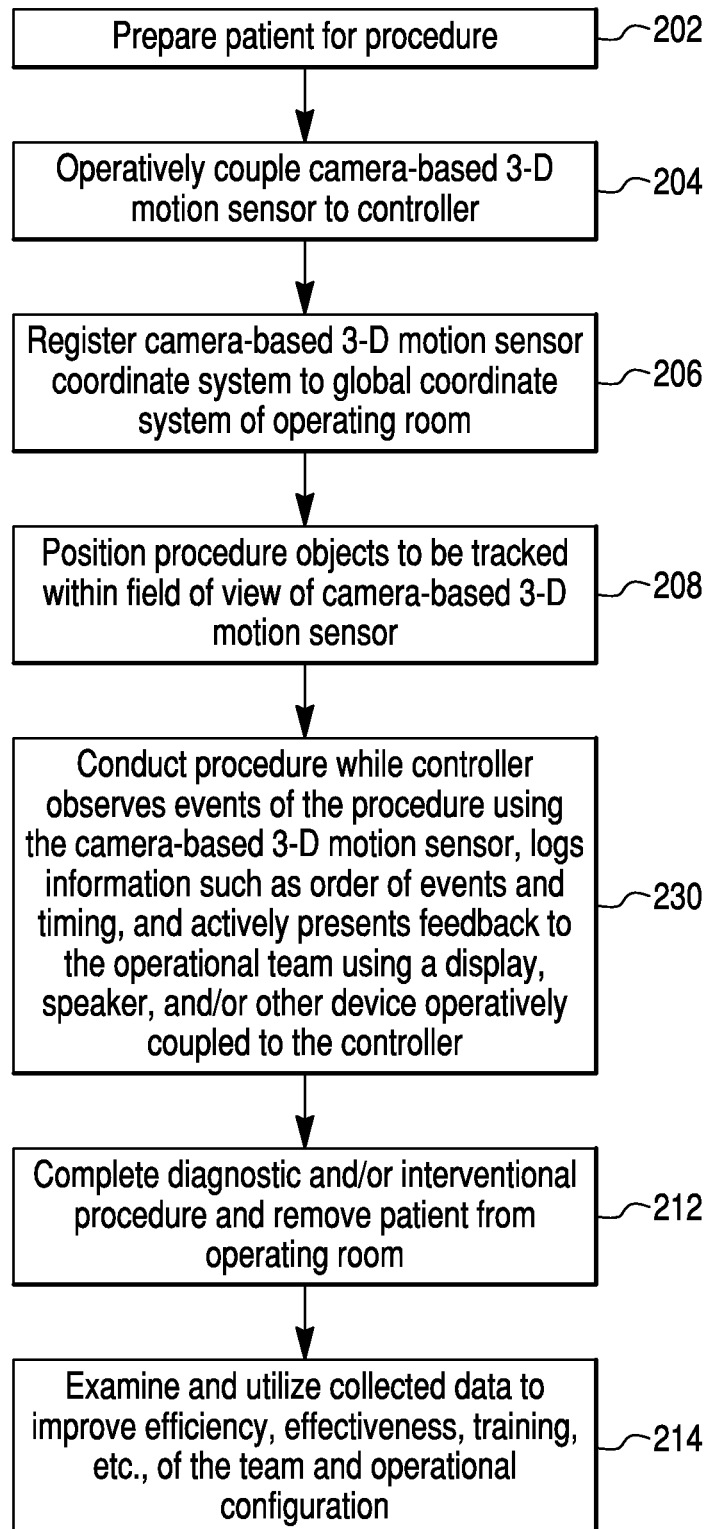
FIG. 5A illustrates a technique for executing a procedure using an integrated system in accordance with the present invention.

Referring to FIG. 5A, in one embodiment, a configuration such as those described above in reference to FIGS. 2A-3C may be utilized in a medical procedure. The embodiment of FIG. 5A differs from that of FIG. 4A in that it includes the active presentation of feedback (230) into the operating room from the controller in an automated fashion during the procedure. For example, in one embodiment, a display intercoupled to a controller may be configured to consistently update a visual presentation of what stage of the predetermined operational protocol, what stage is next, and if anything has been missed. In one embodiment, either a local controller or a master controller may aggregate data and intelligence regarding the particular procedure, and function akin to an IBM Watson type of artificial intelligence system. For example, in one embodiment, the controller may follow along with the procedure, and given its understanding of the patient data, make a recommendation about starting with a smaller tool, different angle, etc.

Referring to FIG. 5B, in one embodiment, a configuration such as those described above in reference to FIGS. 2A-3C may be utilized in a medical procedure. The embodiment of FIG. 5B differs from that of FIG. 4B in that it includes the active presentation of feedback (232) into the operating room from the controller in an automated fashion during the procedure. This embodiment, like that of FIG. 4B, features an identification sensor, and thus enables a more sophisticated opportunity for feedback from the controller. For example, in another variation of the aforementioned IBM Watson type of configuration, the system can identify the physician doing the case and make recommendations to the other attending personnel regarding physician preferences (for example, it can "tell", via the intercoupled monitor, via voice simulation through a speaker, etc., a scrub nurse that Dr Smith always likes to start with a two-sizes down orthopaedic surgery broach, or that Dr Smith always likes to have both A/P and lateral views of a targeted tissue structure before proceeding with any cutting).

Figure 5C:
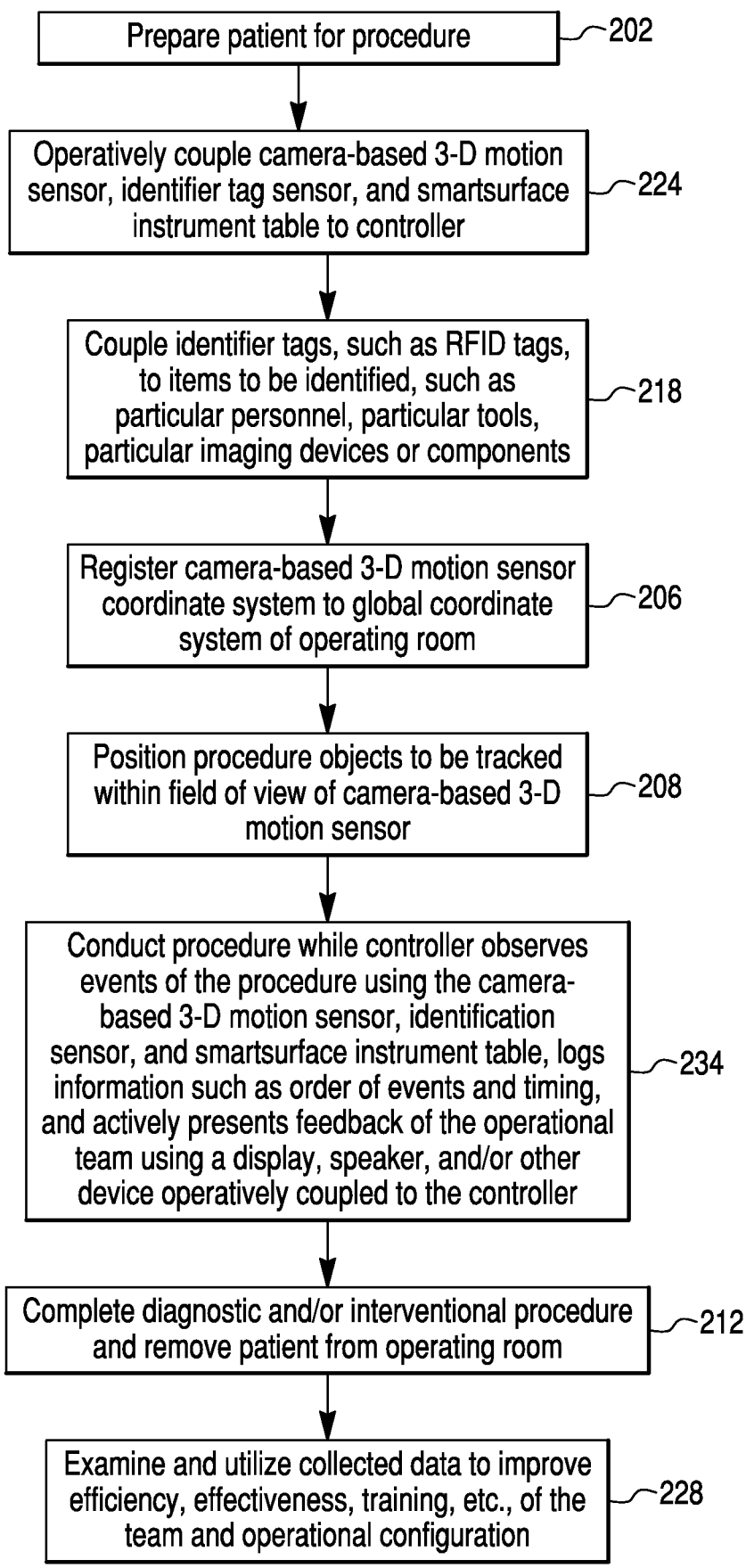
FIG. 5C illustrates a technique for executing a procedure using an integrated system in accordance with the present invention.

Referring to FIG. 5C, in one embodiment, a configuration such as those described above in reference to FIGS. 2A-3C may be utilized in a medical procedure. The embodiment of FIG. 5C differs from that of FIG. 4C in that it includes the active presentation of feedback (234) into the operating room from the controller in an automated fashion during the procedure. With an interconnected smartsurface, the feedback may be dispatched from the controller to the smartsurface as well as to the display or other devices. In a further variation of the aforementioned IBM Watson type of configuration, the example described in reference to FIG. 5B may be expanded to additionally utilize the smartsurface to provide feedback to personnel in the operating room—for example, by communicating the functional equivalent of, "Here—start with this broach, because Dr. Smith likes to start two sizes down" through the means of highlighting or otherwise signaling which item to pick up using the interconnected smartsurface technology.

Figure 6A:
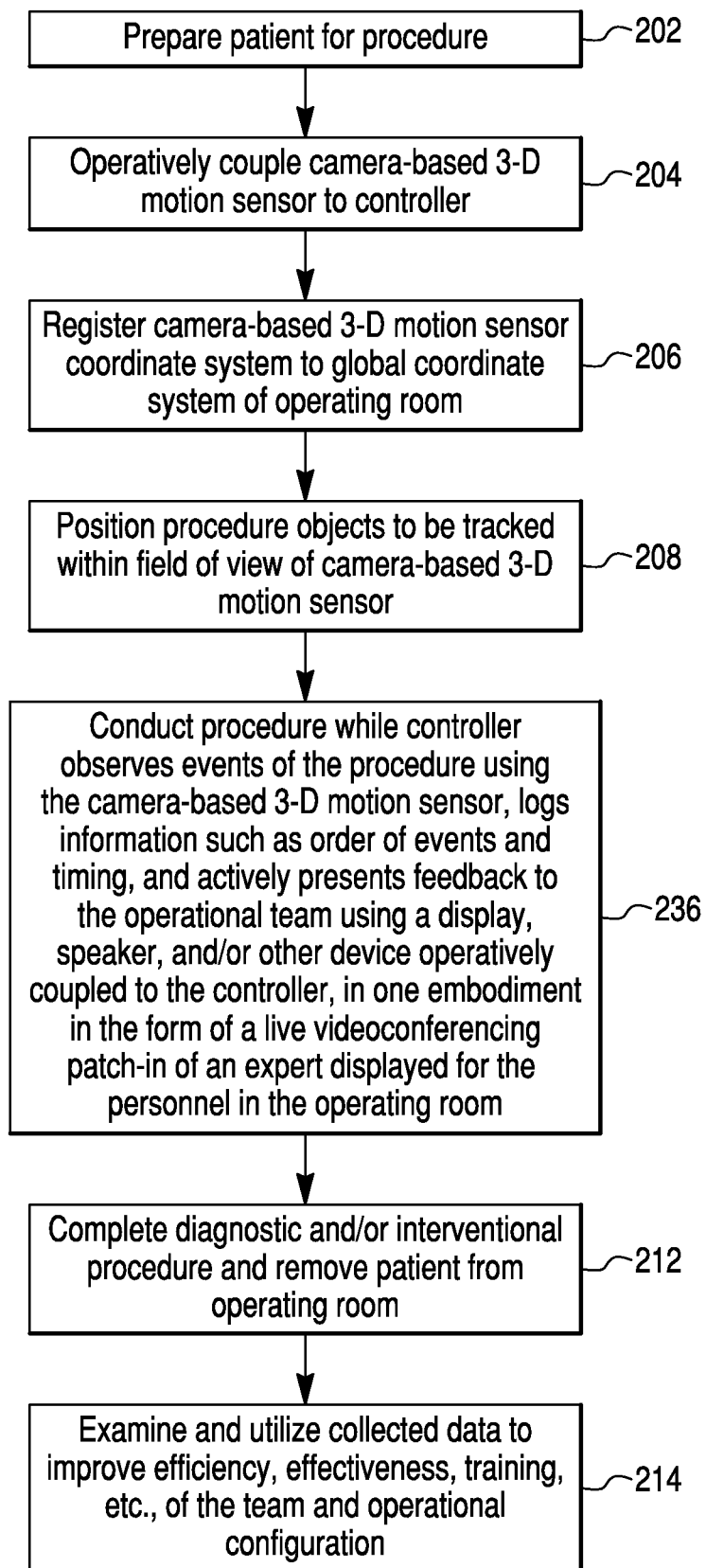
FIG. 6A illustrates a technique for executing a procedure using an integrated system in accordance with the present invention.

Referring to FIG. 6A, in one embodiment, a configuration such as those described above in reference to FIGS. 2A-3C may be utilized in a medical procedure. The embodiment of FIG. 6A differs from that of FIG. 5A in that it includes the active presentation of feedback (236) optionally in the form of a live videoconferencing "patch" which may be presented on the display which may be local to the operating room. Any kind of expert, or even nonexpert, assistance may be functionally brought into the operating room which such a configuration, complements of integrated videoconferencing technology.

Referring to FIG. 6B, in one embodiment, a configuration such as those described above in reference to FIGS. 2A-3C may be utilized in a medical procedure. The embodiment of FIG. 6B differs from that of FIG. 5B in that it includes the active presentation of feedback (238) optionally in the form of a live videoconferencing "patch" which may be presented on the display which may be local to the operating room. Any kind of expert, or even nonexpert, assistance may be functionally brought into the operating room which such a configuration, complements of integrated videoconferencing technology.

Figure 6C:
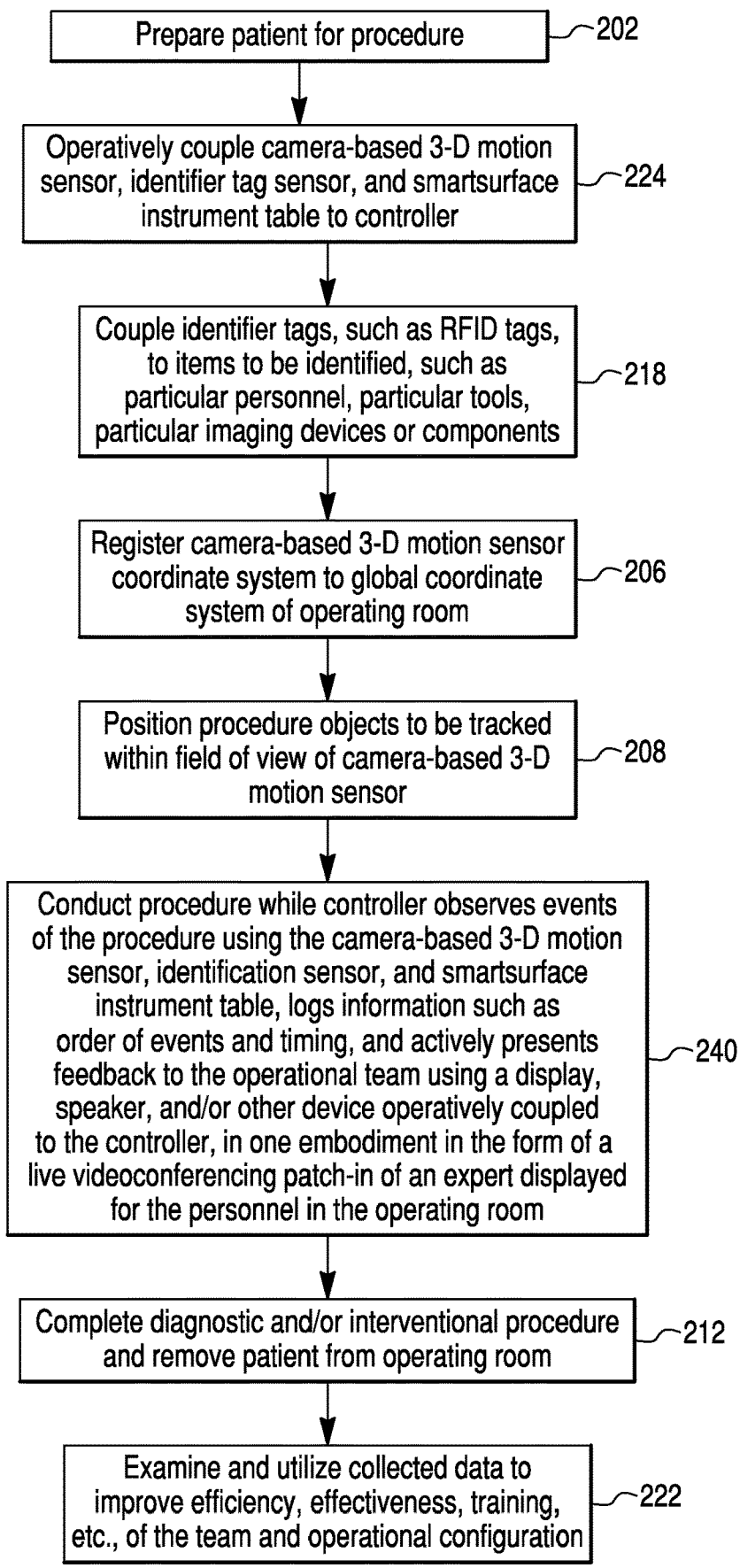
FIG. 6C illustrates a technique for executing a procedure using an integrated system in accordance with the present invention.

Referring to FIG. 6C, in one embodiment, a configuration such as those described above in reference to FIGS. 2A-3C may be utilized in a medical procedure. The embodiment of FIG. 6C differs from that of FIG. 5C in that it includes the active presentation of feedback (240) optionally in the form of a live videoconferencing "patch" which may be presented on the display which may be local to the operating room. Any kind of expert, or even nonexpert, assistance may be functionally brought into the operating room which such a configuration, complements of integrated videoconferencing technology.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject diagnostic or interventional procedures may be provided in packaged combination for use in executing such interventions. These supply "kits" may further include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

The invention claimed is:

1. A system for conducting a procedure in an operating room, comprising:
   a first camera-based 3-D motion sensor mounted in a known position and orientation in a global coordinate system of the operating room and configured to generate signals related to the 3-D position of an object in the operating room based upon a shape of the object relative to the first camera-based 3-D motion sensor; and
   a controller operatively coupled to the first camera-based 3-D motion sensor and configured to:
      define a predetermined operational plan comprising a plurality of positions of the object over time;
      assign a desired time milestone within the procedure for each position of the object in the predetermined operational plan;
      automatically monitor progress of the procedure based at least in part upon one or more positions of the object over time, the one or more positions based at least in part upon the signals from the first camera-based 3-D motion sensor;
      compare the one or more positions of the object over time with the desired time milestone within the procedure for each position of the object in the predetermined operational plan;
      record data relating to an actual time for each position of the object in the predetermined operational plan compared with the desired time milestone; and
      use the data during or after the procedure to provide a recommendation for a change to a future predetermined operational plan.

2. The system of claim 1, wherein the first camera-based 3-D motion sensor comprises a visual spectrum camera.

3. The system of claim 1, wherein the first camera-based 3-D motion sensor comprises an infrared spectrum camera.

4. The system of claim 1, wherein the known position and orientation of the first camera-based 3-D motion sensor relative to the global coordinate system of the operating room is known based upon signals generated from a second sensor configured to generate the signals based upon repositioning or reorientation of the first camera-based 3-D motion sensor relative to an established registration position and orientation of the first camera-based 3-D motion sensor relative to the global coordinate system of the operating room.

5. The system of claim 4, wherein the second sensor comprises an accelerometer.

6. The system of claim 1, wherein the controller is resident in a computing system local to the operating room.

7. The system of claim 1, wherein the controller is resident in a computing system remote to the operating room.

8. The system of claim 1, wherein the controller is further configured to:
   detect a change in the progress of the procedure from the predetermined operational plan; and
   automatically adapt to the change by comparing the progress with a predefined, modified version of the predetermined operational plan that is in accordance with the change and adopting the predefined, modified version of the predetermined operational plan.

9. The system of claim 8, wherein the predefined, modified version of the predetermined operational plan is based at least in part upon a predetermined workflow logic schema.

10. The system of claim 9, wherein the predetermined workflow logic schema is based at least in part upon previous surgical experience.

11. The system of claim 9, wherein the predetermined workflow logic schema is based at least in part upon input from an expert.

12. The system of claim 11, wherein the input from the expert is received from a location remote from the operating room.

13. The system of claim 12, further comprising a video conferencing interface for allowing the expert to visualize and communicate with persons located in the operating room.

14. The system of claim 13, wherein one or more images from the first camera-based 3-D motion sensor are transmitted to the expert over the video conferencing interface using a network connection.

15. The system of claim 1, further comprising:
   one or more identifiers coupled to at least one of: one or more instruments within the operating room, one or more personnel within the operating room, and a patient within the operating room; and
   an identifier sensor communicable with the controller and configured to identify the at least one of the one or more instruments, one or more personnel, and the patient based at least in part upon the one or more identifiers.

16. The system of claim 15, wherein the one or more identifiers are RFID tags and the identifier sensor comprises an RFID sensor.

17. The system of claim 1, further comprising an instrument tracker configured to monitor a position of the object in the operating room based upon detection of radiation reflected by one or more markers coupled to the object, the radiation emitted from the instrument tracker.

18. The system of claim 17, wherein the one or more markers comprise reflective spheres or discs.

19. The system of claim 1, wherein the object is selected from a group consisting of: a surgical instrument, an instrument table, and an operating table.

20. The system of claim 19, wherein the surgical instrument is selected from a group consisting of: a manual surgical hand tool, an electromechanical surgical hand tool, and a pneumatic surgical hand tool.

21. The system of claim 1, wherein the object is an imaging system component selected from a group consisting of: an X-ray source; an X-ray detector; and X-ray source-detector coupling member; an ultrasound transducer; a light source; a light detector; a magnetic field source; and a magnetic field detector.

22. The system of claim 1, further comprising an instrument table comprising an item recognition surface operatively coupled to the controller to facilitate identification of items placed upon the recognition surface.

23. The system of claim 22, wherein the item recognition surface is configured to visually highlight one or more of the items that have been placed upon the item recognition surface.

* * * * *